(12) United States Patent
Amiri

(10) Patent No.: US 9,283,126 B2
(45) Date of Patent: Mar. 15, 2016

(54) DISPOSABLE DIAPER WITH INTEGRATED DISPOSAL AID

(71) Applicant: Mamon Amiri, Irvine, CA (US)

(72) Inventor: Mamon Amiri, Irvine, CA (US)

( * ) Notice: Subject to any disclaimer, the term of this patent is extended or adjusted under 35 U.S.C. 154(b) by 11 days.

(21) Appl. No.: 14/220,141

(22) Filed: Mar. 20, 2014

(65) Prior Publication Data

US 2015/0265476 A1     Sep. 24, 2015

(51) Int. Cl.
*A61F 13/15* (2006.01)
*A61F 13/551* (2006.01)
*A61F 13/84* (2006.01)

(52) U.S. Cl.
CPC ... *A61F 13/5512* (2013.01); *A61F 2013/55125* (2013.01); *A61F 2013/55195* (2013.01); *A61F 2013/8402* (2013.01)

(58) Field of Classification Search
CPC .................. A61F 2013/55125; A61F 13/5512
USPC ........................................ 604/385.06, 385.13
See application file for complete search history.

(56) References Cited

U.S. PATENT DOCUMENTS

| 4,931,052 | A  * | 6/1990  | Feldman ................. | 604/385.06 |
| 5,569,230 | A  * | 10/1996 | Fisher et al. ............. | 604/385.06 |
| 6,454,748 | B1 * | 9/2002  | Ives ........................ | 604/385.06 |
| 2002/0004656 | A1 * | 1/2002 | Khan et al. .............. | 604/385.06 |
| 2004/0092901 | A1 * | 5/2004 | Reece et al. ............. | 604/385.06 |

* cited by examiner

*Primary Examiner* — Jacqueline Stephens
(74) *Attorney, Agent, or Firm* — Ahmadshahi & Associates

(57) ABSTRACT

A disposable diaper is provided which includes a disposal aid containing an integrated cleaning wipe and disposal bag for convenient cleanup and disposal of the diaper after use. The disposable diaper generally comprises a diaper body having a waistband section, an upper fastening element, a crotch section, and a lower fastening element. The disposal aid is positioned adjacent to one of the fastening elements and comprises a pouch having a cleaning wipe compartment and a disposal bag compartment. The cleaning wipe compartment contains a cleaning wipe having a pull tab affixed thereto that protrudes from the wipe compartment and facilitates removal of the cleaning wipe. Similarly, the disposal bag compartment contains a disposal bag having a pull tab affixed thereto that protrudes from the bag compartment and facilitates removal of the bag.

15 Claims, 4 Drawing Sheets

DISPOSABLE DIAPER WITH INTEGRATED DISPOSAL AID

FIELD OF THE INVENTION

The present invention relates to baby care products, particularly wearable diapers.

BACKGROUND OF THE INVENTION

The use of disposable diapers is widespread in the U.S. as well as many other countries. The typical baby goes through 5000 to 8000 diapers before the completion of potty training, and Americans use millions of diapers each year. Obviously, the mess and odor associated with diapers is undesirable and a source of discomfort in the household. Disposable diapers are often thrown directly into the trash, resulting, in an emanating odor in the trash bin. Alternatively, to avoid this, the user must place the dirty diaper in some type of bag prior to placing it in the trash. This however, is inconvenient in that it requires the user to have a supply of such bags and retrieve the bag when needed. Similarly, cleaning wipes are a common tool in cleaning the baby upon unfastening or removal of the diaper, and the user must have a supply of such wipes nearby when needed. There is a need in the art for a disposable diaper that is more amenable to convenient cleanup and disposal.

SUMMARY OF THE INVENTION

A disposable diaper is provided which includes a disposal aid containing an integrated cleaning wipe and disposal bag for convenient cleanup and disposal of the diaper after use. The disposable diaper generally comprises a diaper body having a waistband section, an upper fastening element, a crotch section, and a lower fastening element. The disposal aid is positioned adjacent to one of the fastening elements and comprises a pouch having a cleaning wipe compartment and a disposal bag compartment. The cleaning wipe compartment contains a cleaning wipe having a pull tab affixed thereto that protrudes from the wipe compartment and facilitates removal of the cleaning wipe. Similarly, the disposal bag compartment contains a disposal bag having a pull tab affixed thereto that protrudes from the bag compartment and facilitates removal of the bag.

DETAILED DESCRIPTION

Figure 1:
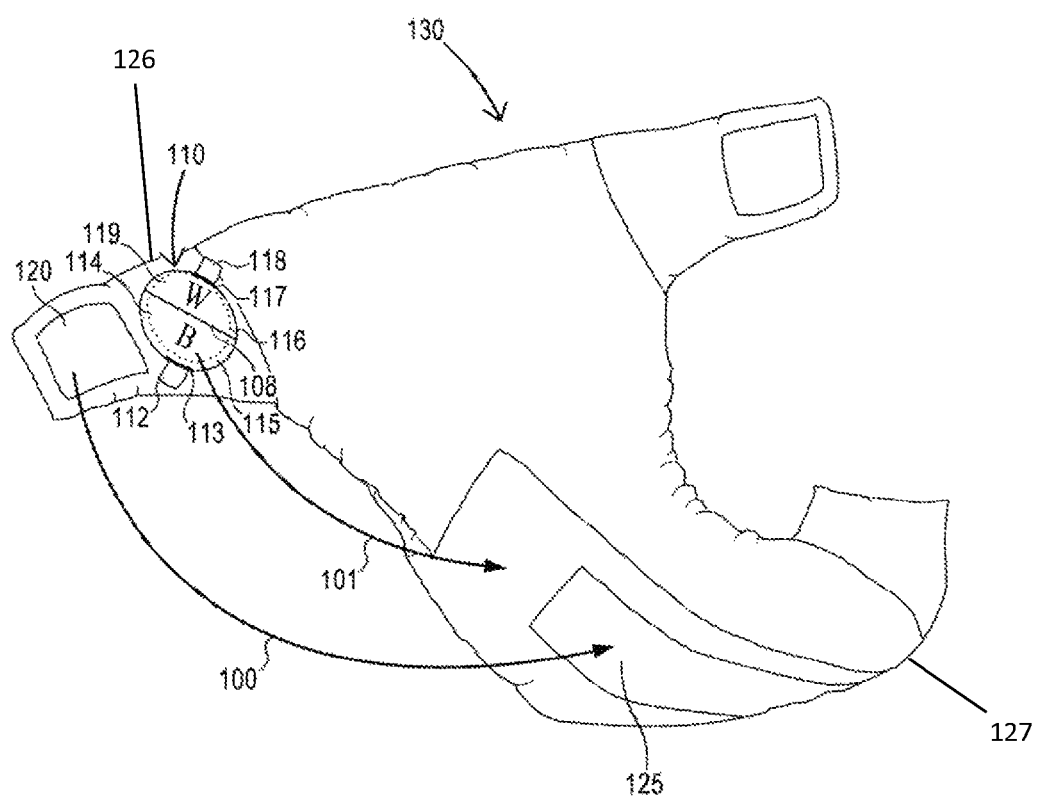
FIG. 1 illustrates a perspective view of the inside of the disposable diaper showing the configuration and position of the cleanup and disposal aid.

The present invention provides a disposable diaper with an integrated cleanup and disposal aid (i.e. "disposal aid") that allows for quick, convenient and sanitary clean up and disposal of the diaper. FIG. 1 illustrates a perspective view of the disposable diaper 130 ("diaper") of the present invention, including a diaper disposal aid 110 affixed to the waistband section of the diaper (i.e. rear end/upper section of the diaper). The overall configuration of the diaper is representative of a typical disposable diaper, which includes a waistband section 126, a crotch section 127, an upper fastening element 120 corresponding to the waistband section, and a lower fastening element 125 corresponding to the crotch area 127. The diaper disposal aid 110 comprises a bag compartment 115 with a disposal bag 114 contained therein (denoted by "B"), and a cleaning wipe compartment 116 (i.e. "wipe compartment") with a disposable cleaning wipe 119 contained therein (denoted by "W"). As shown, the waistband section 126 generally corresponds to the upper portion of the diaper, or the "rear" of the diaper as worn. Similarly, the crotch section 127 generally corresponds to the lower portion of the diaper, or the "front" of the diaper as worn. Thus, the terms "rear" and "frontal" may be used herein to refer to the upper and lower portions of the diaper as shown in FIG. 1, respectively.

Figure 2:
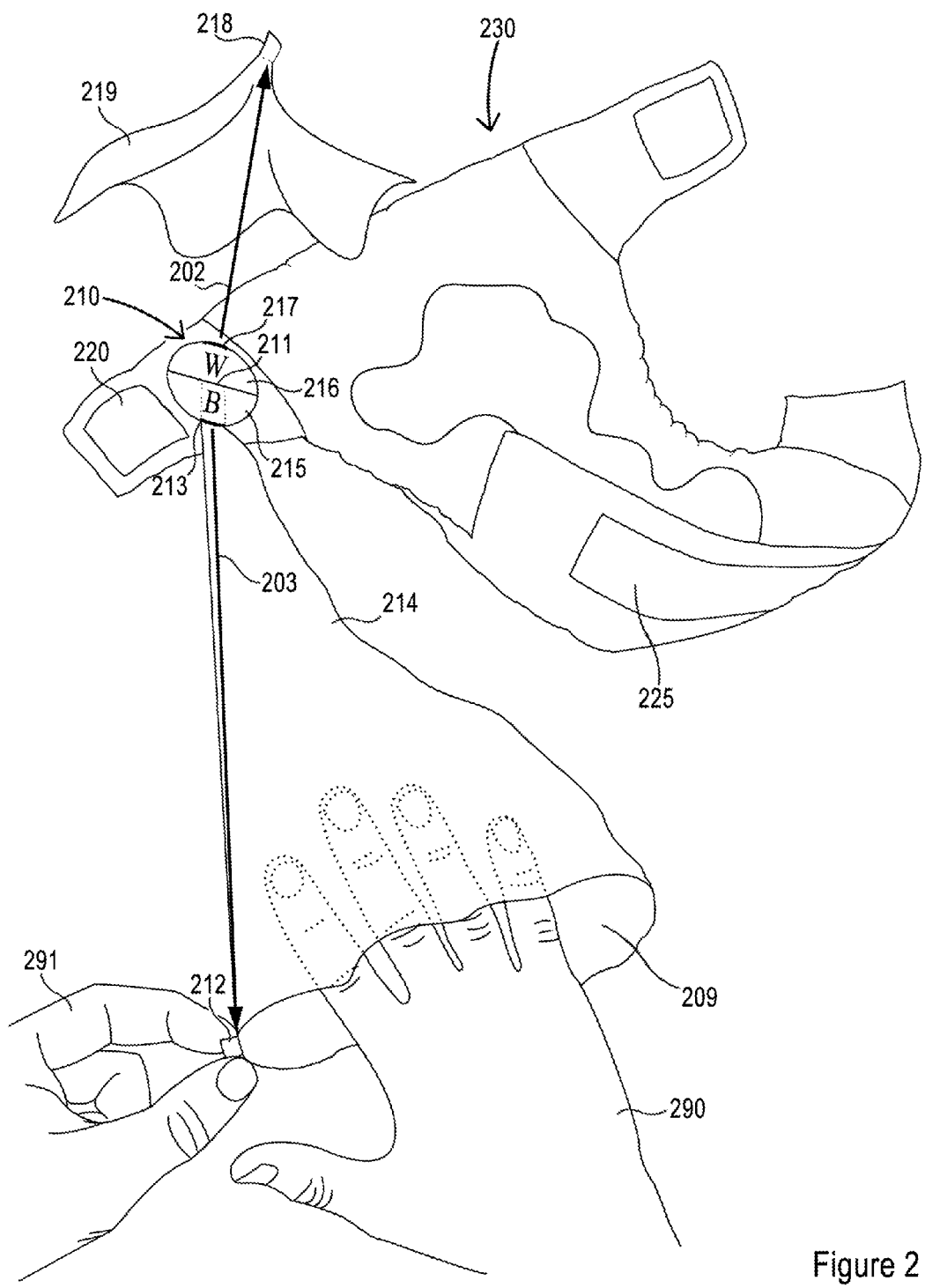
FIG. 2 illustrates a perspective view of the inside of the disposable diaper showing the removal of the cleaning wipe and the disposal bag from their respective containment pouches.

While the representation of the disposal aid 110 in FIG. 1 is that of a circular pouch partitioned into two semispherical compartments, other shapes could be used (e.g. a rectangular pouch partitioned into two rectangular compartments). The cleanup wipe (i.e. "wipe) allows for cleaning of the baby upon opening or removal of the diaper. The disposal bag 114 is used to dispose of the diaper after use. Both the disposal bag and the cleaning wipe are shown with dotted lines, as they lie within their respective pouches and are not visible in this view. The disposal aid 110 is a circular pouch partitioned into two adjoining pouches or compartments, separated by a divider 108. The bag compartment 115 further comprises a bag pull tab 112 and a bag extraction slit 113. The wipe compartment 116 further comprises a wipe pull tab 118 and a wipe extraction slit 117 that facilitate removal oldie cleanup wipe from the pouch. The diaper disposal aid pouch can be made of a disposable material like that of the outer surface of diaper itself, i.e. a plastic or polymer material such as polyethylene. The removal of the cleaning wipe and the disposal bag from the respective pouches is shown in FIG. 2.

The disposal bag is fixed to the inside of the containment pouch at one end in order facilitate easier insertion of the used diaper into the bag (i.e. by placing one's hand into the bag, grabbing the diaper and pulling it reverse the bag). The free end of the disposal bag 114 is connected to and accessed by the bag pull tab 112 which protrudes out of the bag compartment 115 through the bag extraction slit 113, whereas the other end of the disposal bag is fixed to the inside of the bag compartment 115. In the same way, the disposable cleaning wipe 119 is connected to and accessed by the wipe pull tab 118 which protrudes out of the wipe compartment 116 through the wipe extraction slit 117. However, unlike the bag, the cleaning wipe is not fixed to the inside of the pouch, but rather is completely removable, so that it can be used to clean the baby. An advantage of the diaper of the present invention is that the diaper disposal aid 110 can be made separately from the diaper and affixed thereto. In this way, the disposable diaper of the present invention can be made without modifying the manufacturing process for the diaper. Instead, the diaper disposal aid 110 is made separately and simply affixed (e.g. via adhesive) to the diaper body to complete the diaper. Since styles of diaper vary to some degree, the placement and configuration of the diaper disposal aid can be adjusted accordingly. The diaper 130 in FIG. 1 shows a preferred placement of the diaper disposal aid on a standard diaper.

As described above, the cleaning wipe and disposal bag each have a pull tab and are removed from the wipe compartment and bag compartment, respectively, through a slit in their respective compartments. However, other means of removing the contents of the compartments can be utilized while keeping with the spirit of the present invention. For example, instead of a pull tab, an adhesive sticker could cover the extraction slit whereby removing the sticker would expose the slit and allow access to the compartment contents (i.e. the cleaning wipe or disposal bag). An example of such an alternative embodiment is described in connection with FIGS. 4A and 4B below.

Motion arrows 100 and 101 indicate the fastening of the diaper as during placement of the diaper upon the wearer. Via motion arrow 100, a user secures the diaper 130 on the body of the wearer by bringing the upper fastening element 120 (found on the interior surface of the waistband section 126) into contact with the corresponding lower fastening element 125 (found on the exterior surface of the lower fastening element 125 of crotch section 127. The upper fastening element 120 is adjacent to the waistband section 126 of the diaper. The lower fastening element 125 is adjacent to the crotch section 127 of the diaper. These fastening elements are secured upon their contact via standard methods known in the art, such as adhesive or Velcro surfaces. Motion arrow 101 shows the resultant path and destination, of the diaper disposal aid during the aforementioned securing of the diaper denoted by motion arrow 100. The purpose of motion arrow 101 is primarily to illustrate that the diaper disposal aid becomes hidden from view once the diaper is fastened upon the wearer. More specifically, the disposal aid's surface makes contact with a small area adjacent to the lower fastening element 125 near crotch section 127, thus layering it between the waistband section and the crotch section, and making it inaccessible by the wearer (i.e. inaccessible until diaper removal). In this manner, the disposal aid 120 does not make contact with the wearer's skin, is not accessible by the wearer, and cannot become soiled or cause discomfort, which are all important aspects to safe and convenient usage of the disposal aid. Thus, the diaper aid is both safe from access by the wearer, and does not cause discomfort or irritation by contacting the wearer's skin.

FIG. 2 illustrates a perspective view of both disposable cleaning wipe extraction and disposal bag extraction/utilization. The figure depicts a soiled diaper 230 which has been removed from the wearer. Upper fastening element 220 has been detached from or peeled off of lower fastening element 225. In an example of usage, a user may utilize diaper disposal aid 210 by first pulling the wipe pull tab 218 and thereby removing the cleaning wipe 219 from the wipe compartment 216 through the wipe extraction slit 217 as indicated by motion arrow 202. With the cleaning wipe fully extracted from its pouch, it may now be utilized for cleaning the wearer of the diaper as needed. Thereafter, the wipe may be disposed of by placing it in the diaper.

Following use of the wipe, the user can then pull the bag pull tab 212 to remove the disposal bag 214 from the containment pouch 215 through bag extraction slit 213. FIG. 1 shows the removal of the cleanup wipe by a user's left hand 291 as indicated by motion arrow 203. The small portion of the disposal bag remaining within the bag compartment 215 terminates at a bag attachment point 211, anchoring it to the interior of the pouch (via adhesive, stitching or other conventional attachment means). The extracted disposal bag 214 has a bag opening 209 into which a user places their hand (i.e. right hand 290) to grasp the body of the soiled diaper 230 and pull the entire diaper through the bag. This action contains the soiled diaper within the bag by reversing the interior of the bag so that it becomes the exterior. Once a soiled diaper 230 has been contained within the disposal bag 214, the bag may be tied up (sealing the bag opening 209) and/or simply discarded, as desired.

Figure 3:
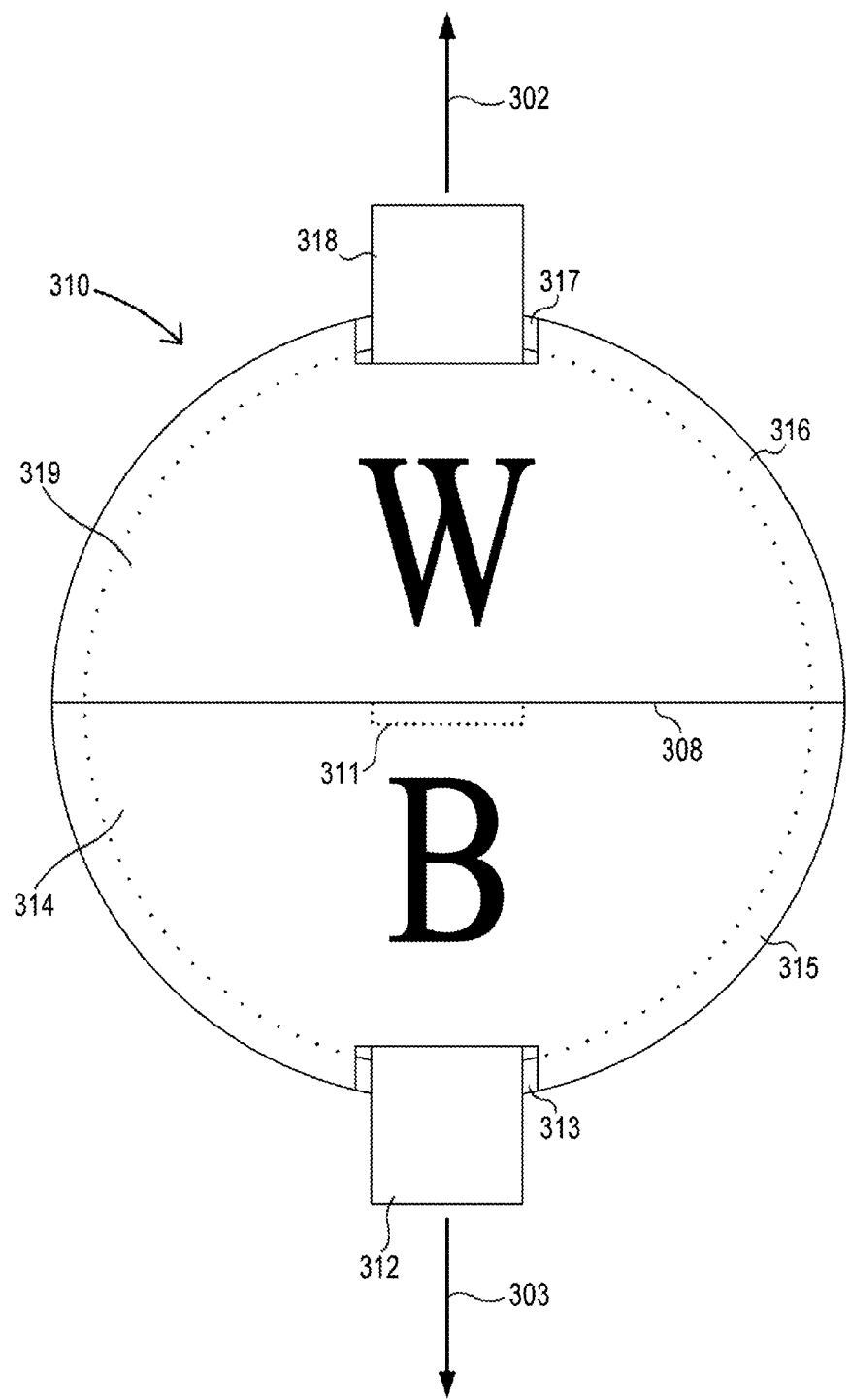
FIG. 3 illustrates a close-up view of the cleanup and disposal aid showing the motion of both the cleaning wipe pull tab and the bag pull tab.

FIG. 3 illustrates a close-up, top view of a diaper cleanup and disposal aid. As discussed above, the disposal aid can be advantageously manufactured in a separate process from that of the diaper and then affixed thereto. The diaper disposal aid 310 comprises a bag compartment 315 (denoted by "B") and a wipe compartment 316 (denoted by "W"). These two pouches are separated by a pouch divider 308. The bag compartment 315 further comprises a disposal bag 314, a bag pull tab 312, and a bag extraction slit 313. The wipe compartment 316 further comprises a disposable cleaning wipe 319, a wipe pull tab 318, and a wipe extraction slit 317. Motion arrow 302 denotes the sliding action of the wipe pull tab 318 which is attached to, and results in the movement of, the disposable cleansing wipe 319 out of the interior of the wipe compartment 316. Similarly, motion arrow 303 denotes the sliding action of the bag pull tab 312 (which is connected to the bag) out from the body of the bag compartment 315 to extract the majority of the disposal bag therefrom. The disposal bag 314 is anchored to the interior bottom edge of the bag compartment 315 via attachment point 311. The cleanup wipe and disposal bag can be stored within their respective pouches via vacuum compression, tight folding, or other means known in the art.

Figure 4:
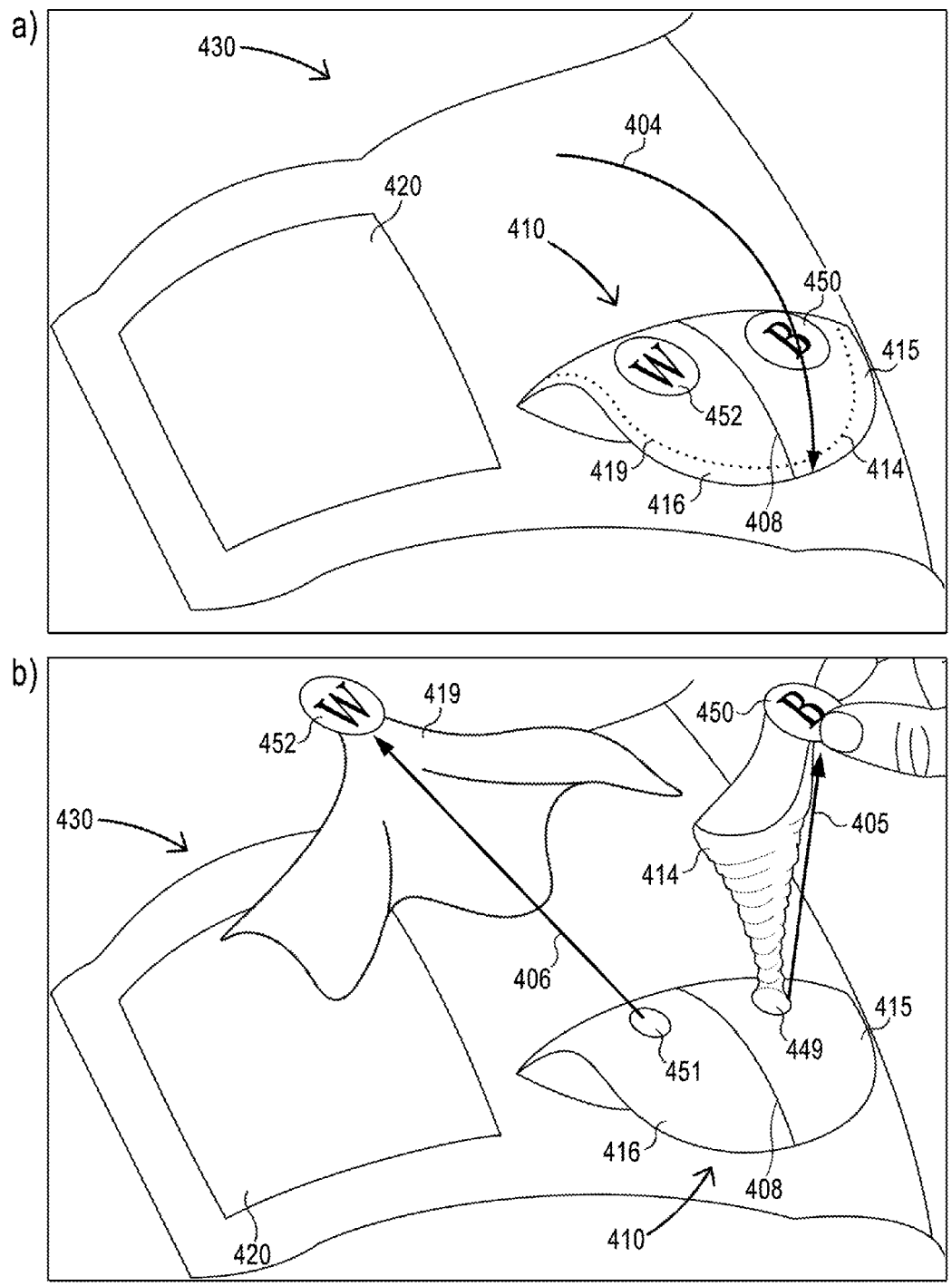
FIGS. 4A and 4B illustrate an alternate embodiment of the diaper disposal aid utilizing a peel away mechanism for extraction of both the disposable cleaning wipe and the disposal bag from the interior of the cleanup and disposal aid.

FIGS. 4A and 4B illustrate an alternate embodiment of a diaper disposal aid which presents an alternate means of removing the disposable cleaning wipe and disposal bag from the containment pouch. As in the previous embodiment, the diaper disposal aid 410 comprises two adjoining compartments—a wipe compartment 416 and a bag compartment 415, each separated by the pouch divider 408. As shown in FIG. 4A, unique to this embodiment is the method of first peeling the diaper disposal aid 410 away from the waistband section of the diaper 430 in order to access the contents of the pouch. In this embodiment, the disposal aid 410 is positioned adjacent and interior to the upper fastening element 420. Motion arrow 404 shows the action of peeling away the disposal aid, and consequently revealing the underbelly of the disposal aid (the surface previously adhered to the diaper surface)—which possesses a bag access sticker 450 (shown with a "B" on its surface), and a wipe access sticker 452 (shown with a "W" on its surface). It may be useful to have the disposal aid peel away approximately 75 percent of the sticky portion of its surface from the diaper, thereby leaving it attached to the diaper by a small area for a more streamlined, efficient approach to disposal. This echoes the permanent attachment method of the primary embodiment of the invention. In this embodiment, the disposal aid may be manufactured with the diaper in such a way that it is partially attached in a permanent way to the diaper, e.g. via sewing or alternative method known in the art. As with the primary embodiment, the diaper disposal aid is placed in a location adjacent to upper fastening element 420, obscuring it from view and making it strategically difficult to reach during wearer usage.

FIG. 4B illustrates that, after peeling the disposal aid 410 away from the diaper, a user may grab or pinch the aforementioned access stickers and pull them away (upward in this figure) from the underbelly surface of the disposal aid. With respect to the cleaning wipe 419, this action is carried out via motion arrow 406. Similarly, the disposal bag 414 is extracted via motion arrow 405. Using a method similar to that of the primary embodiment of the invention, the access stickers are attached permanently to their respective sanitation/disposal aids. As such, when (for example) the wipe access sticker 452 is peeled away from its wipe compartment 416, it causes wipe extraction as a secondary consequence. Similarly, when the bag access sticker 450 is peeled away from its bag compartment 415, it causes bag extraction as a secondary consequence. The majority of the bag is extracted through the bag extraction hole 449, which was previously covered by the bag access sticker 450 in FIG. 4A. As in the initial embodiment of the invention, the extracted bag is permanently affixed to the interior of its pouch by an anchor point, whereas the extracted wipe is fully removable from its pouch. Concerning both bag and wipe, the surface of an access sticker that adheres itself to a containment pouch possesses a ring of adhesion surrounding its center—the point at which the bag or wipe is connected. Thus, FIGS. 4A and 4B depict a disposal aid in which the cleaning wipe compartment and disposal bag compartment each contain an opening that is covered by an adhesive tab that can be removed to access the compartment. Moreover, the opening of the cleaning wipe compartment and disposal bag compartment faces the diaper surface such that the disposal aid pouch must be peeled away from the diaper surface in order to access the respective compartments.

While there have been described herein what are considered to be preferred and exemplary embodiments of the present invention, other modifications of the invention shall be apparent to those skilled in the art from the teachings herein. For example, the relative dimensions of device may be altered while keeping within the spirit and teachings of the invention. It is therefore desired to be secured, in the appended claims all such modifications as fall within the spirit and scope of the invention.

What is claimed is:

1. A disposable diaper comprising:
   a diaper body having a waistband section, an upper fastening element adjacent to said waistband section, a crotch section, and a lower fastening element adjacent to said crotch section;
   a disposal aid adjacent to said upper fastening element, said disposal aid having a top surface operable to contact an area adjacent to the lower fastening element thus sandwiching said disposal aid between the waistband section and the crotch section thereby making the disposal aid inaccessible by a wearer of the disposable diaper, said disposal aid comprising a pouch having a cleaning wipe compartment and a disposal bag compartment;
   wherein the cleaning wipe compartment contains a cleaning wipe with a pull tab affixed thereto, said pull tab protruding from a slit in the wipe compartment and facilitating the removal of the cleaning wipe from the wipe compartment; and
   wherein the disposal bag compartment contains a disposal bag with a pull tab affixed thereto, said pull tab protruding from a slit in the bag compartment and facilitating the removal of the bag from the bag compartment.

2. The disposable diaper of claim 1, wherein a closed end of the disposal bag is affixed to the disposal bag compartment.

3. The disposable diaper of claim 1, wherein the disposal aid is made of polyethylene.

4. The disposable diaper of claim 1, wherein the disposal aid is circular.

5. A disposable diaper comprising:
   a diaper body having a waistband section, a crotch section, and a fastening element;
   a pouch affixed to the diaper, said pouch having a top surface operable to contact an area adjacent to the fastening element thus sandwiching said pouch between the waistband section and the crotch section thereby making the pouch inaccessible by a wearer of the disposable diaper, said pouch comprising a cleaning wipe compartment and a disposal bag compartment;
   wherein the cleaning wipe compartment contains a cleaning wipe with a pull tab affixed thereto, said pull tab protruding from a slit in the wipe compartment and facilitating the removal of the cleaning wipe from the wipe compartment; and
   wherein the disposal bag compartment contains a disposal bag with a pull tab affixed thereto, said pull tab protruding from a slit in the bag compartment and facilitating the removal of the bag from the bag compartment.

6. The disposable diaper of claim 5, wherein a closed end of the disposal bag is affixed to the disposal bag compartment.

7. The disposable diaper of claim 5, wherein the pouch is made of polyethylene.

8. The disposable diaper of claim 5, wherein the pouch is circular.

9. A diaper disposal aid comprising:
   a disposal aid pouch configured to be affixed to a diaper, said diaper having a diaper body, said diaper body having a waistband section, a crotch section, and a fastening element, said pouch having a top surface operable to contact an area adjacent to the fastening element thus sandwiching said pouch between the waistband section and the crotch section thereby making the pouch inaccessible by a wearer of the disposable diaper, said pouch further comprising a cleaning wipe compartment and a disposal bag compartment;
   wherein the cleaning wipe compartment contains a cleaning wipe that can be removed from the compartment and used for cleaning; and
   wherein the disposal bag compartment contains a disposal bag for disposal of the diaper after use.

10. The diaper disposal aid of claim 9, wherein the disposal aid pouch is made of polyethylene.

11. The diaper disposal aid of claim 9, wherein the disposal aid pouch is circular.

12. The diaper disposal aid of claim 9, wherein the cleaning wipe compartment and disposal bag compartment each contain an opening that is covered by an adhesive tab that can be removed to access the compartment.

13. The diaper disposal aid of claim 9, further comprising:
   a pull tab affixed to the cleaning wipe, said pull tab protruding from a slit in the wipe compartment and facilitating the removal of the cleaning wipe from the wipe compartment; and
   a pull tab affixed to the disposal bag, said pull tab protruding from a slit in the bag compartment and facilitating the removal of the bag from the bag compartment.

14. The diaper disposal aid of claim 9, wherein a closed end of the disposal bag is affixed to the disposal aid pouch.

15. The diaper disposal aid of claim 9, wherein the disposal aid pouch is affixed to the diaper such that it must be peeled away from the diaper in order to access the cleaning wipe compartment and the disposal bag compartment.

* * * * *